(12) United States Patent
Hwang et al.

(10) Patent No.: US 8,154,058 B2
(45) Date of Patent: Apr. 10, 2012

(54) BIO-SENSOR AND METHOD OF MANUFACTURING THE SAME

(75) Inventors: Gyu Weon Hwang, Seoul (KR); Wook Seong Lee, Seoul (KR); Jeung-hyun Jeong, Seoul (KR); Jong-Keuk Park, Seoul (KR); Young Joon Baik, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 458 days.

(21) Appl. No.: 12/589,622

(22) Filed: Oct. 23, 2008

(65) Prior Publication Data

US 2010/0065892 A1      Mar. 18, 2010

(30) Foreign Application Priority Data

Mar. 3, 2008   (KR) .................. 10-2008-0019699

(51) Int. Cl.
*H01L 23/58*  (2006.01)
*H01L 27/14*  (2006.01)
(52) U.S. Cl. ....................... 257/253; 257/414
(58) Field of Classification Search .......... 257/253, 257/E21.409, E29.255, 414; 977/774
See application file for complete search history.

(56) References Cited

U.S. PATENT DOCUMENTS

| | | | |
|---|---|---|---|
| 5,777,372 A * | 7/1998 | Kobashi .................. | 257/414 |
| 2006/0120918 A1* | 6/2006 | Fukutani et al. .......... | 422/57 |
| 2007/0231211 A1 | 10/2007 | Yoo et al. | |

FOREIGN PATENT DOCUMENTS

| | | |
|---|---|---|
| JP | 7050419 | 2/1995 |
| JP | 8240555 | 9/1996 |
| KR | 100773549 | 10/2007 |

OTHER PUBLICATIONS

Wensha Yang et al, "Fabrication and characterization of a biologically sensitive field-effect transistor using a nanocrystalline diamond thin film" Applied Physics Letters vol. 85 No. 16, Oct. 18, 2004.

Jung-Hoon Yang et al. "Characterization of Direct Immobilized Probe DNA on Partially Functionalized Diamond Solution-Gate Field-Effect Transistors" Japanese Journal of Applied Physics vol. 45, No. 42, 2006, pp. L1114-L1117.

Yang et al., Wensha; "Fabrication and characterization of a biologically sensitive field-effect transistor using a nanocrystalline diamond thin film", Applied Physics Letters vol. 85 No. 16, Oct. 18, 2004.

Yang et al., Jung-Hoon; "Characterization of Direct Immobilized Probe DNA on Partially Functionalized Diamond Solution-Gate Field-Effect Transistors", Japanese Journal of Applied Physics vol. 45, No. 42, 2006, pp. L1114-L1117.

* cited by examiner

*Primary Examiner* — Hung Vu
(74) *Attorney, Agent, or Firm* — Ladas & Parry LLP (57) ABSTRACT

A bio-sensor includes a gate dielectric formed on a silicon semiconductor substrate, a gate electrode of a conductive diamond film formed on the gate dielectric, probe molecules bonded on the gate electrode for detecting biomolecules, and source/drain regions formed on the semiconductor substrate at the sides of the gate electrode. The gate electrode is a comb shape or a lattice shape.

27 Claims, 12 Drawing Sheets

BIO-SENSOR AND METHOD OF MANUFACTURING THE SAME

FIELD OF THE INVENTION

The present invention relates to a bio sensor using diamond gate silicon channel (DGSC) semiconductor device and, more particularly, to a bio sensor in which biocompatible diamond is employed to remarkably improve lifespan, reuse, and stability of the bio-sensor, and in which a field effect transistor (FET) structure without using diamond as a channel region thereof is employed so that sensitivity of the bio-sensor can be improved and a silicon (Si) electronic circuit is integrated therewith, and a manufacturing method thereof.

BACKGROUND OF THE INVENTION

In recent, bio-sensors such as DNA chip and protein chip use a label type fluorescence method to measure biomolecules in which the biomolecules are measured through fluorescence material, labeling. However, such label type method causes structural and functional changes of the biomolecules during the labeling process. Since the florescence method depends on optical signals to obtain data, it is difficult to apply semiconductor electronics technology to the bio-sensor. Further, there is problem in that the size of an optical measuring device is large to be portable or to embed in other systems.

Thus, a field effect transistor (FET) type bio-sensor capable of utilizing merits of a non-label type method and of combining micro-electronics and nano-technology is more excellent than currently widely used bio-sensors and sensors in above-mentioned technical view.

The above-mentioned conventional silicon semiconductor-based FET bio-sensor is advantageous in terms of utilizing a well-developed silicon process, but has a poor bonding characteristic between silicon and biomolecules. In order to overcome these problems, in the conventional art, to utilize the excellent bond characteristics of gold-sulfur (Au—S), a method of bonding thiol-groups (—SH) to biomolecules and then bonding the bonded product to gold thin film on a surface of the silicon is used.

However, the bonding of Au—S also has the following disadvantages. First, since Au is a typical contamination material to be avoided in a manufacturing line of semiconductors, it is difficult to utilize conventional manufacturing lines of semiconductor devices. Therefore, it is difficult to enter the market. Secondly, in a case of bonding the thiol-group to proximal ends of biomolecules, there is concern about deformation and loss of function of sensitive molecules such as protein.

Finally, the conventional bonding of Au—S has poor stability and a short life-span because it is easily affected by oxidation. These problems result in a relatively short shelf-life and restrictions for storage and transportation. Recently, a new bio-sensor technology using diamond thin film is on the rise. This technology has superior stability and shelf-life compared to that using the conventional Au—S bond because diamond and the biomolecules form carbon (C)-carbon (C) covalent bonds. Since the conventional diamond-based bio-sensor employs poly-crystalline diamond thin film as a conductive channel, defects such as grain boundaries contained in poly-crystalline diamond remarkably decrease mobility of carriers in comparison to conventional silicon semiconductor devices so that the conventional diamond-based bio-sensor does not have a performance superior to a Si-based bio-FET sensor using gold that has been researched. Such low mobility of carriers is a fatal drawback in forming a peripheral electronic circuit of a sensor to be coupled with micro-electronics. Moreover, there is a solution gate FET (SG-FET) bio-sensor using a diamond surface as a channel, however, since the SG-FET bio-sensor depends on only surface conduction of the diamond thin film, the adjustment of a channel by controlling a gate voltage is not possible, thus sensitivity of a sensor for biomolecules is not good. Moreover, the SG-FET mainly uses a way of measuring a change of pH due to reaction between biomolecules and enzymes to indirectly quantify biomolecules rather than directly detecting the biomolecules. Thus, there is a high risk of noise being mixed with a measured signal and a high possibility of malfunction of the sensor. Thus, there is required a new bio-sensor configuration capable of utilizing both of excellent bonding stability between biomolecules and diamond, and excellent channel characteristics of the silicon FET.

SUMMARY OF THE INVENTION

It is, therefore, an object of the present invention to provide a new bio-sensor for overcoming drawbacks of a conventional bio-sensor, that is, having lifespan and stability superior to those of an Si-FET bio-sensor using thiol groups and a measurement sensitivity superior to that of a conventional FET bio-sensor using diamond, and a manufacturing method thereof.

In accordance with an aspect of the present invention, there is provided A bio-sensor including: a gate dielectric formed on a silicon semiconductor substrate; a gate electrode of a conductive diamond film formed on the gate dielectric; probe molecules bonded on the gate electrode for detecting biomolecules; and source/drain regions formed on the semiconductor substrate at the sides of the gate electrode.

In accordance with another aspect of the present invention, there is provided a A bio-sensor including: a gate dielectric of non-conductive diamond thin film formed on a silicon semiconductor substrate; a gate electrode formed on the gate dielectric partly exposing the gate dielectric; probe molecules bonded on the exposed gate electrode for detecting biomolecules; and source region/drain region formed on the semiconductor substrate at the sides of the gate electrode.

In accordance with still another aspect of the present invention, there is provided a A method of manufacturing a bio-sensor, including: (a) forming a gate dielectric on a silicon semiconductor substrate; (b) forming a gate electrode by forming a conductive diamond layer on the gate dielectric and patterning the conductive diamond layer; (c) forming a source region and a drain region at sides of the gate electrode on the semiconductor substrate; and (d) bonding probe molecules for detecting biomolecules to the gate electrode.

The present invention relates to a bio-sensor and a manufacturing method thereof. In other words, according to the present invention, a gate of a FET bio-sensor is manufactured using a diamond thin film having excellent biocompatibility so that lifespan, reuse, and stability of a sensor are remarkably improved and implements a field effect transistor (FET) structure excluding the diamond from a channel region, different from a conventional diamond-based bio-sensor employing the diamond in the channel region, to improve the sensitivity, and the bio-sensor can be integrated with a silicon (Si) electronic circuit.

BRIEF DESCRIPTION OF THE DRAWINGS

The above and other objects and features of the present invention will become apparent from the following description of embodiments given in conjunction with the accompanying drawings, in which.

DETAILED DESCRIPTION OF THE PREFERRED EMBODIMENTS

Hereinafter, embodiments of the present invention will be described in detail with reference to the accompanying drawings.

According to the technical point of the present invention, a gate of a field effect transistor (FET) bio-sensor is manufactured using a diamond thin film with excellent biocompatibility so that life span, reuse, and stability of a sensor are remarkably improved and a field effect transistor (FET) structure excluding diamond from a channel region is implemented to improve sensitivity of a sensor, resulting in easily achieving the object and features of the present invention.

Generally, FETs are classified into a MOSFET, a MESFET, a JFET, and so forth. A bio-sensor in accordance with an embodiment of the present invention employs the MOSFET as a basic structure thereof because the gate of the MOSFET is capable of conveniently controlling the current between drain and source. Further, the MOSFET devices are classified into a depletion mode device and an enhancement mode device according to its operational mode. The enhancement mode type FET is employed as the basic structure. Hereinafter, all MOSFETs mentioned in the description indicate the enhancement mode MOSFET.

Figure 1:
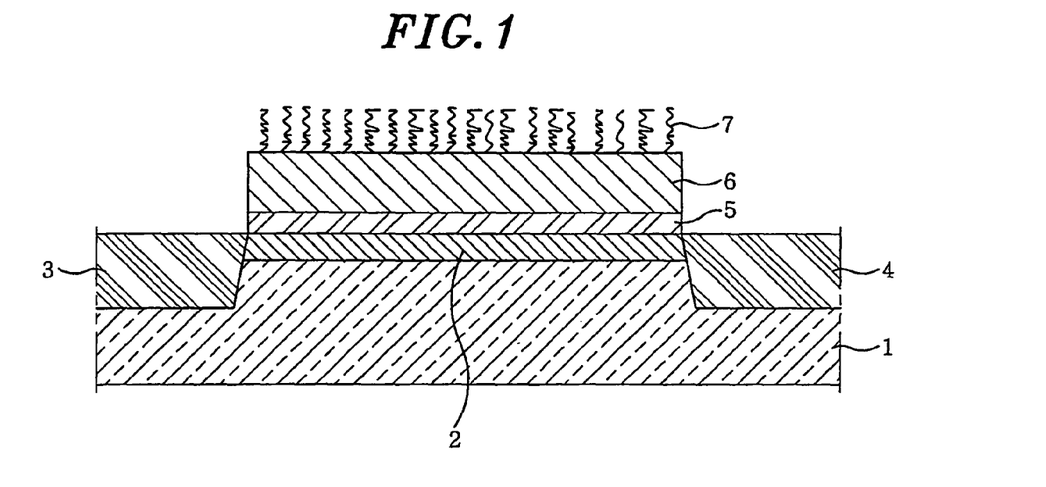
FIG. 1 is a cross sectional view illustrating a MOSFET bio-sensor in accordance with an embodiment of the present invention.

FIG. 1 is a cross sectional view schematically illustrating a configuration of a MOSFET that is a basic structure of a bio-sensor in accordance with an embodiment of the present invention, where diamond is used as a gate material to bond thereto biomolecules such as probe molecules.

Figure 9A:
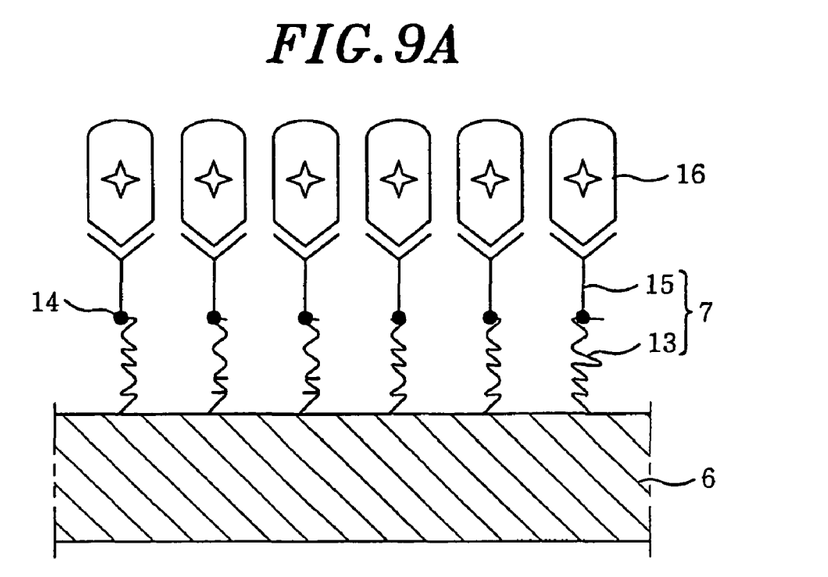
FIGS. 9A and 9B are a view illustrating a detection of an target biomolecules from the bio-sensor in accordance with the embodiment of the present invention.
Figure 9B:
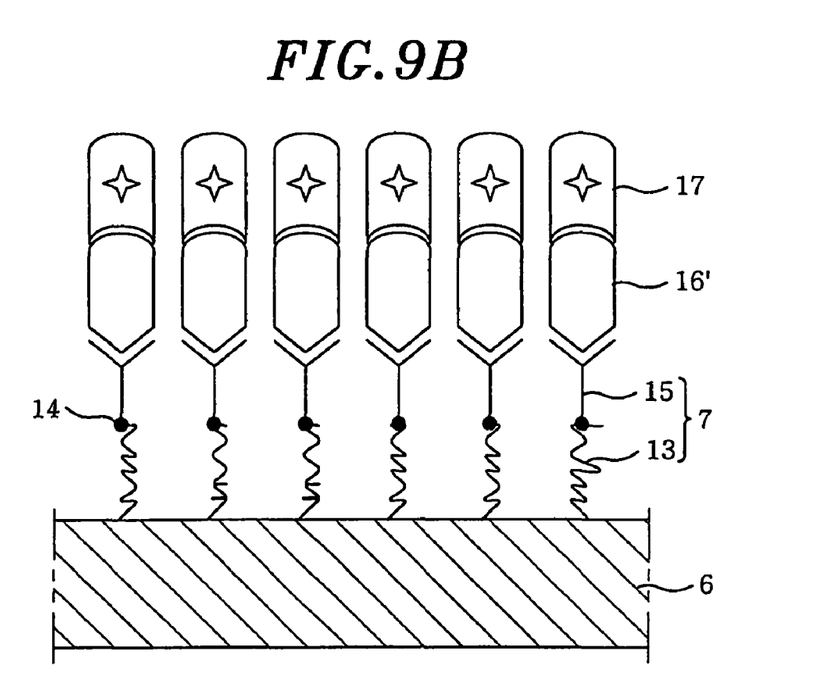

As shown in FIG. 1, the bio-sensor in accordance with the embodiment of the present invention includes a channel region 2, a gate dielectric 5, a source region 3, a drain region 4, and a gate electrode 6, on top of a single crystal silicon (Si) semiconductor substrate 1. The channel 2, the source 3, the drain 4, and the gate dielectric 5 made from silicon dioxide of the bio-sensor device of the embodiment of the present invention have identical configuration to those of a MOSFET used as a switching device. However, the configuration of the bio-sensor device is different from those of the MOSFET used as a switching device in that the gate electrode 6 is made of a conductive diamond thin film. Such conductive diamond thin film used in the gate electrode 6 is the most important feature of the present invention, and has function to reliably fix probe molecules 7 to a surface thereof by carbon-carbon covalent bonds such that the bio-sensor detects biomolecules as well as normal function to adjust conductivity of the channel region 2 by apply thereto a gate voltage so as to induce depletion and inversion of electrical charges and so forth to the channel region 2. The probe molecules 7, as shown in FIGS. 9A and 9B, include adapter molecules 13 bonded to the surface of the diamond thin film and detecting molecules 15 (cDNA, antibody, protein, and the like) for actually detecting the biomolecules. The probe molecules 7 include linker bond or crosslinking molecules 14 for bonding the adapter molecules 13 and the detecting molecules 15. Since the diamond gate is employed in the silicon-based MOSFET in accordance with the embodiment of the present invention, it enables the channel to be controlled, which is important to the sensitivity of detecting the biomolecules, thereby obtaining higher SNR than conventional diamond-based SG-FET using an electrode in an electrolyte solution (solution gate) instead of a gate electrode.

Further, the C—C bond between carbons forming the diamond and back-bone carbons of the biomolecules (probe molecules) is much stronger than conventional Au—S bond. Since the C—C bond does not need a specific functional group such as a thiol group, a structural change of the biomolecules, generated when attaching the functional group, does not occur, different from the conventional Au—S bond. Accordingly, in comparison to the conventional bio-sensor utilizing Au-thiol bond, the bio-sensor in accordance with the embodiment of the present invention solves the life span and stability problems of the conventional bio-sensor while maintaining an advantage of easily integrating with silicon-based semiconductor electronics. In other words, since the probe molecules 7 are directly attached to the surface of the gate electrode 6 made of the diamond thin film, the stability of biomolecules can be significantly improved as compared to an attachment using the conventional Au—S bond.

Meanwhile, ISFET (ion-sensitive FET) is conventional FET type bio-sensor using diamond, in which a substrate is made of diamond so that a channel region is made of diamond. Unlike a single crystalline diamond, a poly-crystalline diamond has defects such as grain boundaries. Therefore, a mobility of charge carriers of the poly-crystalline diamond thin film is much lower than that of a silicon film. Further, the diamond has a band gap Eg of 5.5 eV, which is much higher than 1.1 eV of silicon. Furthermore, in case that boron B used as dopant is doped in the diamond, most dopants are not activated at room temperature. Accordingly, in addition to the problem of the mobility, there are many restrictions of using the diamond as a semiconductor channel at room temperature. Therefore, the FET type bio-sensor using diamond loses the primary merit of the general FET type bio-sensor, i.e., capability of being integrated with existing electronic circuitry, and thus the FET type bio-sensor using the diamond as a channel has no substantial advantage over other types of bio-sensors such as cantilever type bio-sensors, optical type bio-sensors, and the like. The bio-sensor in accordance with the embodiment of the present invention is configured such that only the gate electrode 6 is made of diamond without changing the single crystal silicon 1 used for the source 3, the drain 4, and the channel 2 to utilize the excellent channel characteristics of the single crystal silicon, thereby solving above-mentioned problems.

When detecting biomolecules using the conventional diamond ISFET bio-sensor, the biomolecules to be detected (hereinafter, referred to 'target biomolecules') are reacted with enzymes to generate reaction products causing pH changes, e.g., an acid ($H^+$), bases ($OH^-$, $NH_3$), or the like, then the diamond ISFET bio-sensor detects a change of quantity of the reaction products. In this case, pH of human body fluids is different by person so that there is a problem of quantification of a detected signal even when a measurement is performed within a buffer solution, and the problems are even greater from the fact that the pH of the human body fluid is variable according to other erroneous reasons, noise, and the like. In other words, since the biomolecules are indirectly measured, there are several issues due to the measuring method. Conversely, the bio-sensor in accordance with the embodiment of the present invention directly detects electrostatic effect of the biomolecules to be detected, therefore, the above-mentioned problem can be overcome.

Figure 2A:
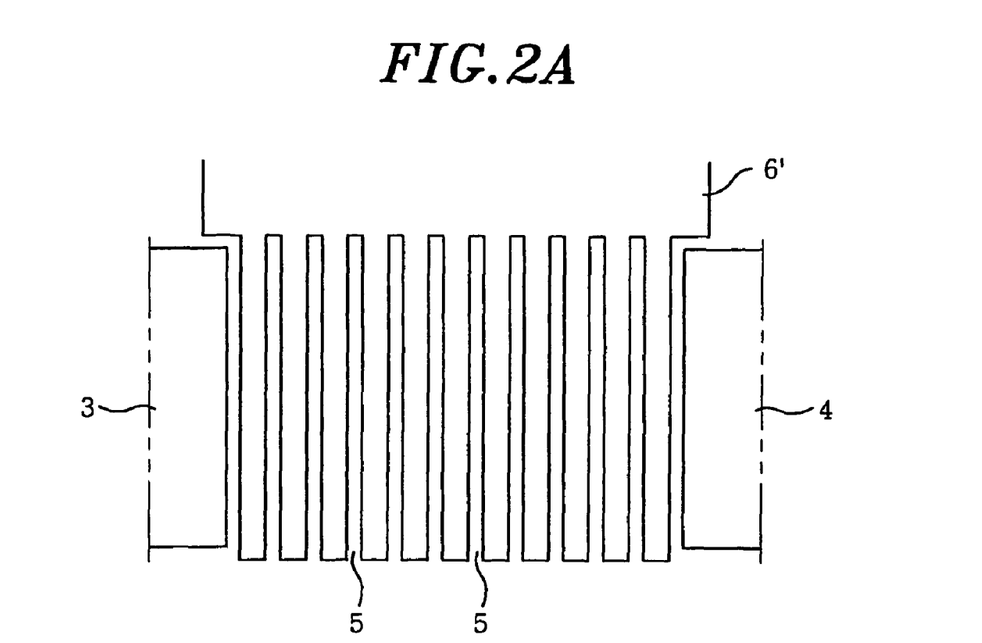
FIGS. 2A and 2B are views illustrating an example of a comb-shaped or a lattice-shaped gate electrode in accordance with an embodiment of the present invention.
Figure 2B:
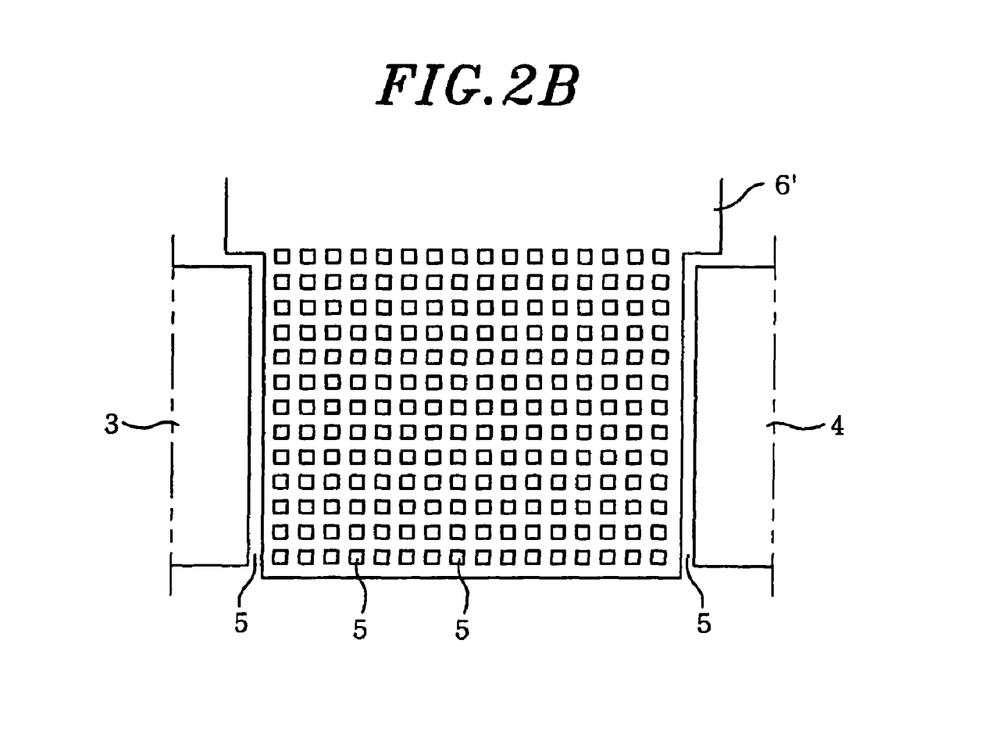

In the bio-sensor of the embodiment of the present invention, the diamond gate electrode 6 has a comb shape as shown in FIG. 2A or a lattice shape as shown in FIG. 2B.

Figure 3:
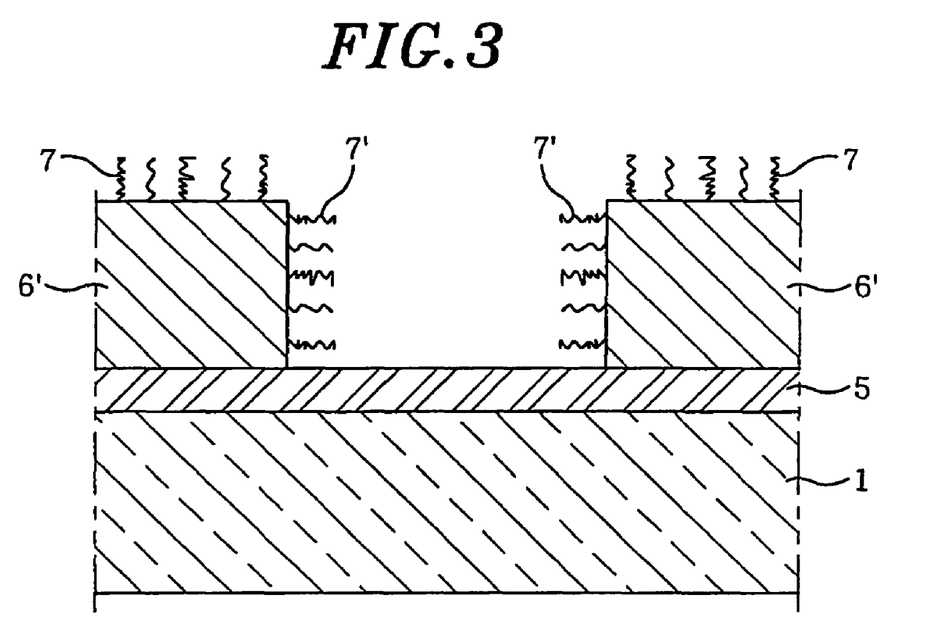
FIG. 3 is a view illustrating an example of a comb-shaped or a lattice-shaped gate electrode to which probe molecules are attached in accordance with an embodiment of the present invention.

In the bio-sensor in accordance with the embodiment of the present invention having the gate electrodes of FIGS. 2A and 2B, as shown in FIG. 3, probe molecules 7 and 7' are attached not only to an upper surface of the gate electrode 6' but also to side walls of the gate electrode 6'. The probe molecules 7' attached to the side walls of the gate electrode 6' are much closer to the gate dielectric 5 and the channel 2 than the probe molecules 7 attached to the upper surface of the gate electrode 6'. Thus, in comparison to a case of the probe molecules attached to the upper surface of the gate electrode 6', the intensity of a signal, from the electrostatic effect of the biomolecules bonded to the probe molecules, transmitted to the gate dielectric 5 and the channel 2, is much greater, thereby increasing the sensitivity of the bio-sensor. From the top view of the comb-shaped or lattice-shaped gate electrode, it can be understood that some of a surface of the gate dielectric 5 is exposed to the lower side of the comb-shaped or lattice-shaped gate electrode as shown in FIGS. 4A and 4B.

Figure 4A:
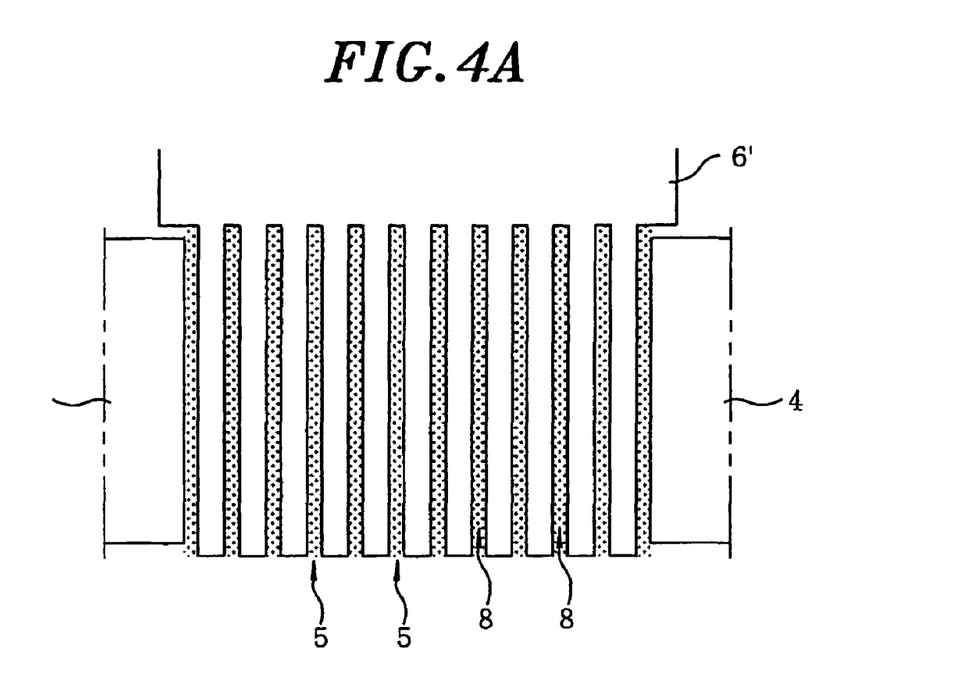
FIGS. 4A and 4B are views illustrating a configuration of a comb-shaped or a lattice-shaped sensor with a diamond nano dot complex gate in accordance with an embodiment of the present invention.
Figure 4B:
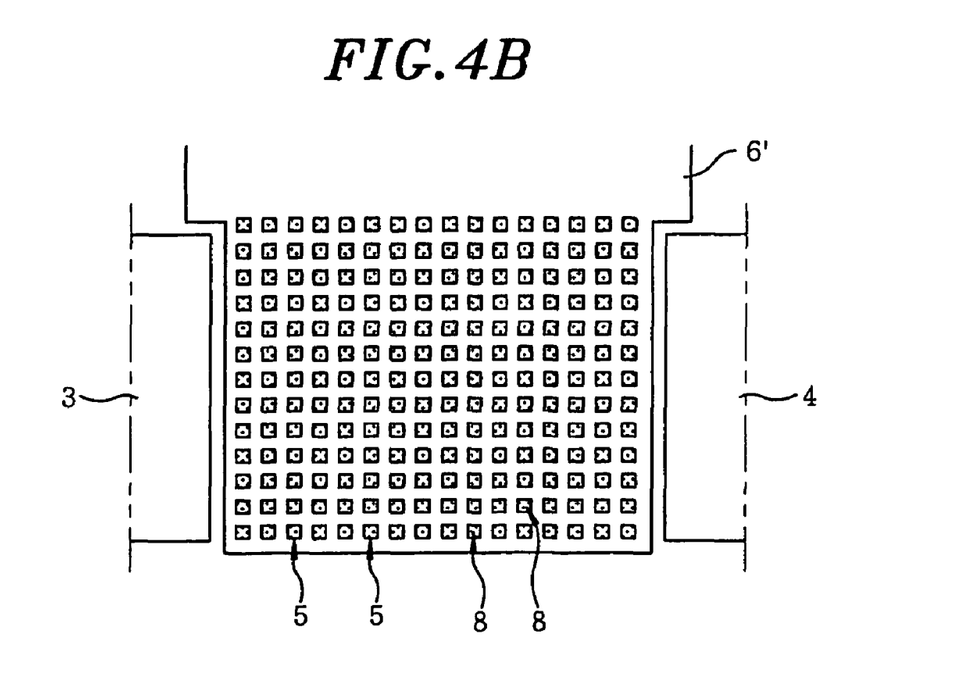

In the bio-sensor in accordance with the embodiment of the present invention, as shown in FIGS. 4A and 4B, dot-shaped nano-crystalline (NC) diamond 8 with a nano-degree radius is chemical vapor deposited on the surface of the exposed gate dielectric 5 to be used as a site for attaching the probe molecules. Since the chemical vapor deposition of nano-dot NC-diamond is well known in the art and can be implemented by simply increasing the density of a nucleation site from nucleation of an early stage of the chemical vapor deposition, the chemical vapor deposition of nano-dot NC-diamond is convenient process without need for lithography process and in this chemical vapor deposition the size of the nano-dots can be easily controlled within a range of several nm to several tens of nm by controlling the time for the chemical vapor deposition. Since the surface area increases in the nano-dot structure of the present invention, electrostatic influence of charges of target biomolecules becomes greater in the channel so that the sensitivity of the sensor increases.

Next, will be described a method of improving the detection sensitivity of the bio-sensor by increasing controllability of the gate voltage with respect to the source-drain current flowing through the channel 2 in the FET. Firstly, a conventional typical method of improving the gate controllability with respect to the channel is of using material with a high dielectric constant (high-k) as the gate dielectric, and those materials with high dielectric constant are usually oxides such as $HfO_2$, $ZrO_2$, $TiO_2$, and $Al_2O_3$ and nitrides such as $SiN_x$. However, since the material with a high dielectric constant directly contacts the silicon channel 2 when the material with a high dielectric constant is used as the gate dielectric 5, interface defects, e.g., charge trapping are generated and thus the characteristics of the channel 2 are deteriorated.

Figure 5:
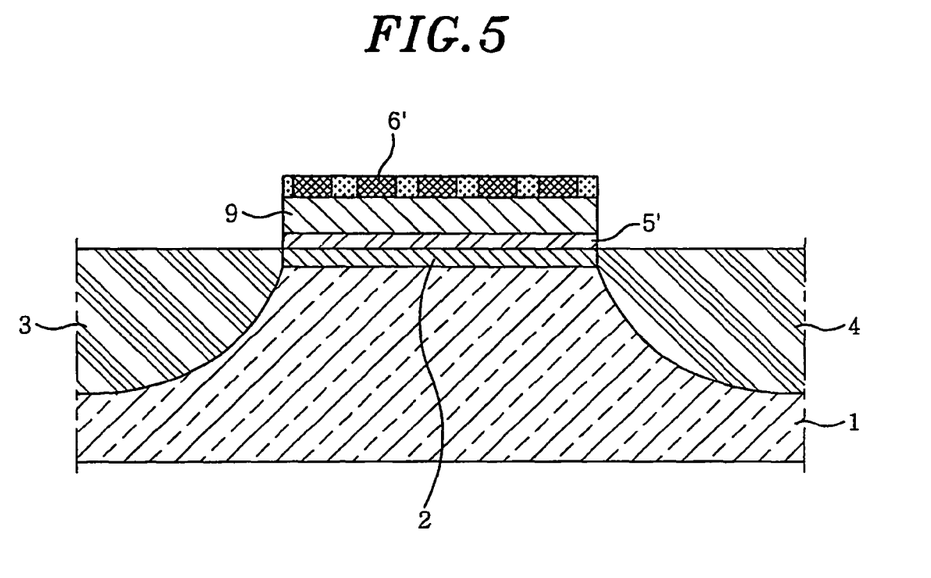
FIG. 5 is a cross sectional view of a sensor having a multi-layer gate dielectrics in accordance with an embodiment of the present invention.

FIG. 5 illustrates configuration of a bio-sensor having multiple gate dielectrics in accordance with another embodiment of the present invention, and the bio-sensor in FIG. 5 is substantially the same as those illustrated in FIGS. 1 and 2 but is different in that the gate dielectric 5 shown in FIGS. 1 and 2 is in the form of a dual layer with a silicon oxide layer 5' and a high-k or a nonconductive diamond thin film dielectric 9 which are sequentially laminated.

To solve the above-mentioned problem of channel characteristics deterioration, as illustrated in FIG. 5, a multiple layer configuration in which firstly the silicon oxide layer ($SiO_2$) 5' is formed directly on the silicon channel 2 and the dielectric 9 with a high dielectric constant such as the above-mentioned nitride layer is laminated thereon or a complex layer such as $HfSiO_x$ and $HfSiO_xN_y$ is used to maintain the advantage and to reduce drawbacks of the dielectric with the high dielectric constant. In this case, since the dielectric is an oxide or nitride, its bonding characteristics with respect to the biomolecules are poor. Therefore, instead of directly attaching the biomolecules to the dielectric, like the case of using silicon oxide layer $SiO_2$, the dielectric 9 is laminated with the diamond gate 6 to bond the biomolecules on the diamond gate 6 to be used as a bio-sensor.

Moreover, the nonconductive diamond thin film may be used in the dielectric 9 instead of the material with a high dielectric constant so that the biomolecules are attached to exposed surfaces of the nonconductive diamond thin film. The dielectric constant of the nonconductive diamond thin film is increased higher than that of the silicon oxide layer ($SiO_2$) so that the advantage of the dielectric with a high dielectric constant is kept. Further, the bonding between the above mentioned exposed surfaces and the biomolecules is secured. The diamond thin film may be formed to have various resistances, i.e., to be a conductor or insulator by controlling variables when the diamond thin film is synthesized, and the dielectric constant thereof can be adjusted to be equal to or greater than that of the silicon oxide layer according to the size of the grain.

Figure 6A:
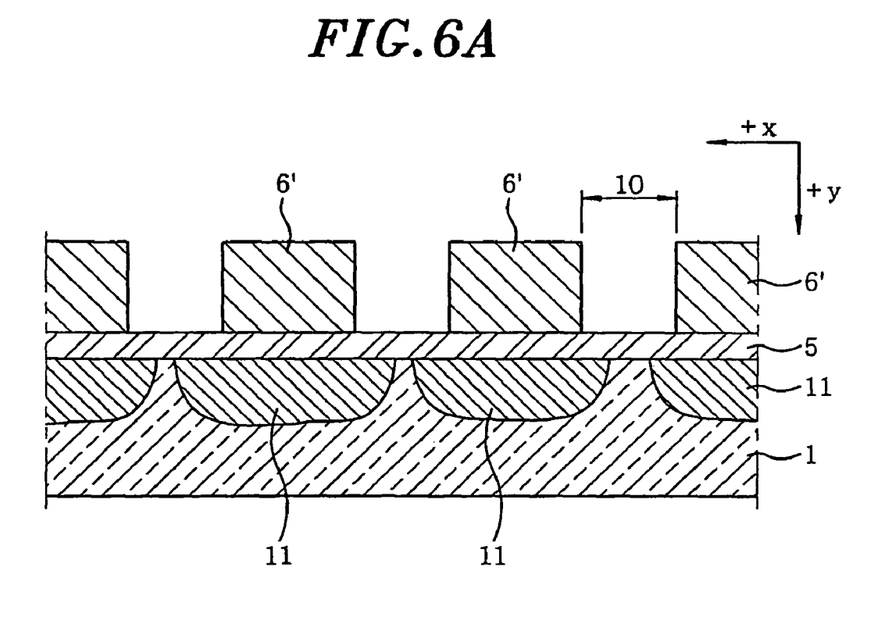
FIGS. 6A and 6B are exemplary views illustrating operation of a FET in a comb-shaped or a lattice-shaped gate structure in accordance with an embodiment of the present invention.
Figure 6B:
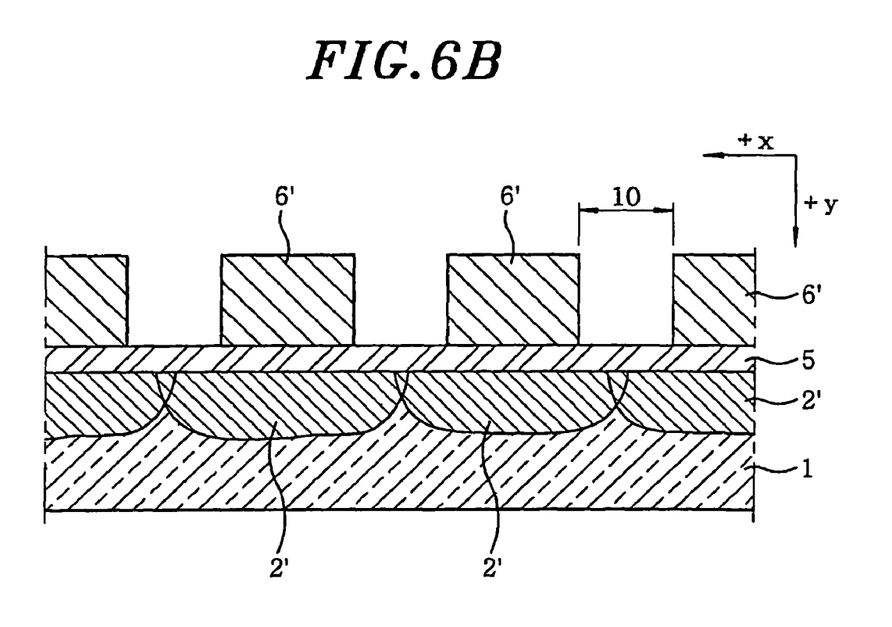

In this case, the silicon oxide layer 5' reduces density of charge traps generated in the interface between silicon (Si) of the channel 2 and the nonconductive diamond film dielectric 9 with a high dielectric constant. Probe molecules may be directly fixed to exposed portions of the nonconductive diamond dielectric 9. In this case, since positions to which the probe molecules are fixed are closer to the channel 2 than positions where the probe molecules are fixed to the side wall and the nano-dots 8 (See FIGS. 4A and 4B) of the gate electrode 6', detection of higher sensitivity is enabled. Moreover, in this case, wherein many more biomolecules, than those in the method, described with reference to FIG. 4A or 4B, of laying out the nano-dots 8 in order to attach more biomolecules close to the exposed surface of the gate dielectric, are attached thereto, the sensitivity of the bio-sensor can be more increased. FIGS. 6A and 6B are schematic views illustrating a method of maximizing a signal to noise ratio (SNR) of the bio-sensor by controlling an X-direction gap 10 between the teeth of comb or the strips of lattice in the FET bio-sensor with a comb-shaped or lattice-shaped gate electrodes in accordance with the embodiment of the present invention.

When a voltage is applied to the gate electrode 6' of a MOSFET, a depletion region 11 is generated in the silicon substrate under the gate electrode 6'. When a voltage higher than a threshold voltage $V_{th}$ is applied, the depletion region 11 is changed into an inversion layer to function as the channel 2. When the gate voltage is applied, the depletion region 11 in the silicon substrate widens in the +Y-direction, thereby forming a channel with a specific depth. The depletion region 11 increases in ±X-direction from both ends of the gate electrode as much as the increased quantity in the +Y-direction. In the comb-shaped or lattice-shaped gate, an initial depletion region 11 increases as the gate voltage increases, then becomes inversion layer, thereby forming the channel. Further, depletion regions 11, not connected to each other in the initial state as shown in FIG. 6A, increase in the X-direction as the gate voltage increases so that they are connected to each other to form the channel 2' as shown in FIG. 6B. Furthermore, the gap 10 between the teeth of comb or the strips of lattice can be adjusted such that the depletion regions 11 are not connected to each other before target biomolecules are attached, but, when the target biomolecules are attached, the depletion regions 11 are connected to each other due to the influence of charges of the target biomolecules and then become inversion layer, thereby forming the channels 2'. Therefore, a bio sensor having distance 10 adjusted as such has increased sensitivity so that target biomolecules with low concentration are detected.

Such distance 10 is inversely proportional to a root of a doping concentration of the silicon substrate. The gap 10 may range from 2.0 micrometers to 2.2 micrometers when general substrate doped to a concentration of $10^{15}/cm^3$ is used.

Hereinafter, variation of the sensitivity of the bio-sensor according to the gap of the gate electrodes as shown in FIGS. 6a and 6B will be described in detail. In order to maximize the sensitivity of the bio-sensor in the comb-shaped or the lattice-shaped gate structure, the gap between the teeth of comb or the strips of lattice needs to be within a preset range. The gap needs to be adjusted such that the depletion regions generated when the gate voltage are connected together only when the biomolecules are detected whereas the depletion regions are not connected when the biomolecules are not connected. The variation of the depletion regions is determined by a function of the doping concentration of the channel region and surface potential, and the maximum width $W_T$ of the depletion regions of a p-type semiconductor can be approximately expressed by the following equation 1 using known semiconductor theory.

$$W_T = \sqrt{\frac{2K_S \varepsilon_0}{qN_A} \Phi_s} \qquad \text{Equation 1}$$

where, $K_S$ is a dielectric constant of a silicon substrate, $\varepsilon_0$ is a dielectric constant of a vacuum, q is a unit charge, $N_A$ is a doping concentration of a channel region, and $\Phi_S$ is surface potential. Since $\Phi_S$ is expressed with respect to the doping concentration by the following equation 2, actual $W_T$ can be expressed by a function depending on only the doping concentration.

$$\Phi_s = 2\frac{kT}{q}\ln\left(\frac{N_A}{n_i}\right) \qquad \text{Equation 2}$$

where, k is the Boltzmann constant, T is absolute temperature, and $n_i$ is intrinsic carrier concentration of a silicon substrate. When combining the two equations, the following equation 3 is obtained.

$$W_T = \sqrt{\frac{2K_S\varepsilon_0}{qN_A}\left(\frac{2kT}{q}\right)\ln\left(\frac{N_A}{n_i}\right)} = \frac{2}{q}\sqrt{\frac{K_S\varepsilon_0}{N_A}kT\ln\left(\frac{N_A}{n_i}\right)} \qquad \text{Equation 3}$$

Figure 7A:
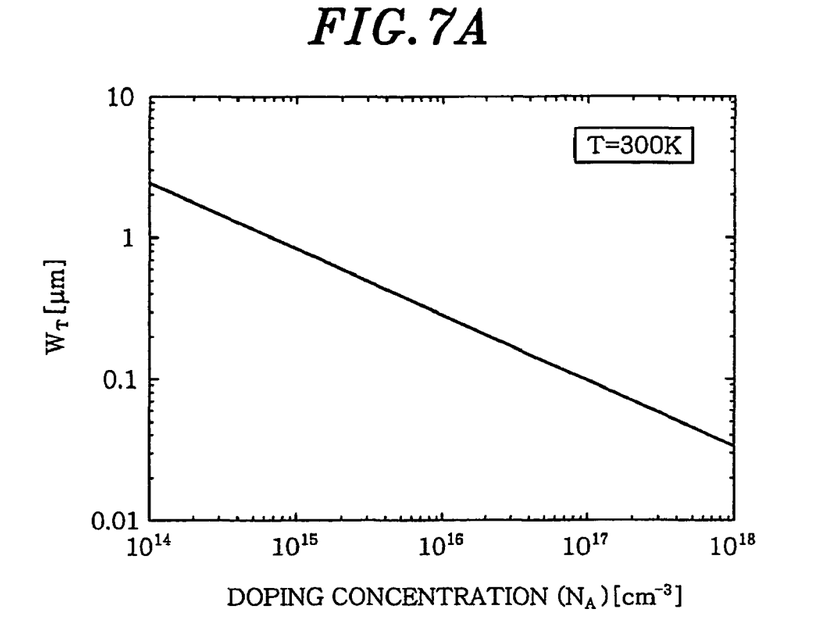
FIGS. 7A and 7B are graphs illustrating a correlation between a maximum width and a doping concentration of a depletion region and a correlation between a gap between teeth of comb and a subthreshold swing (SS) in accordance with an embodiment of the present invention.

Therefore, an approximate gap between the teeth of comb or the strips of lattice can be obtained through the doping concentration $N_A$ of the channel regions. As shown in FIG. 7a, the distance decreases as the doping concentration increases. Since the maximum width $W_T$ is 1.1 micrometers at the concentration of $10^{15}/cm^3$, the gap between the teeth of comb or strips of the strips of lattice need to be adjusted within a range of 2 micrometers to 2.2 micrometers twice the maximum width $W_T$.

The sensitivity of the bio-sensor may be determined by finding out how large a signal $\Delta V_G$ is generated by a single biomolecule bonded to the surface thereof and by finding out how much output variation $\Delta I_D$ is induced by the generated signal $\Delta V_G$ at the outside of the bio-sensor. The former is determined by a function of the surface of the diamond and the design of the detecting molecules, and the latter is determined by the design of the semiconductor device. Here, only the letter of the sensitivity is considered. Since an inverse number of a subthreshold swing SS, defined as follows, among characteristics evaluating the FET device has the same meaning as an initial sensitivity of the latter, the SS is taken as an index of the sensitivity.

$$SS = \left(\frac{\partial \log I_D}{\partial V_G}\right)^{-1} \qquad \text{Equation 4}$$

Figure 7B:
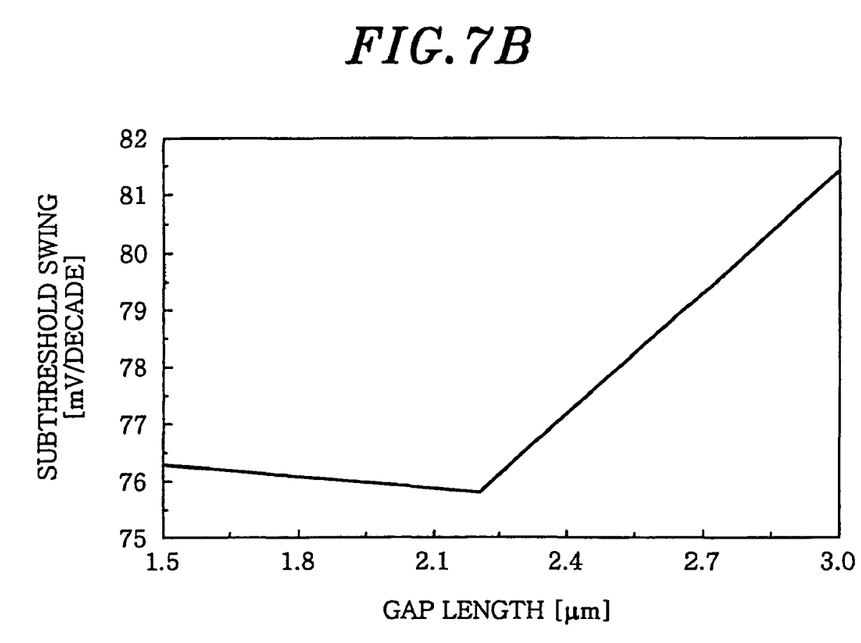

SS has been calculated when using a silicon substrate and a diamond substrate, respectively, each doped to a concentration of $10^{15}/cm^3$. SS is 210 mV/decade in a case of using the diamond substrate as the channel and 76 mV/decade in a case of using the silicon substrate as the channel, i.e., it requires a 210 mV of gate voltage variation due to the detected biomolecules in order to increase an initial current by 10 times when using the diamond substrate as the channel but only a 76 mV of the gate voltage variation is required in a case of using the silicon substrate as the channel. This means that a high output signal $\Delta I_D$ can be obtained even from a low initial signal $\Delta V_G$. In case of using a gate electrode of comb shape, When SS is depicted by gaps between the teeth of comb, it can be understood, as shown in FIG. 7B, that SS gradually increases until the gap reaches 2.2 micrometer, two times the maximum width $W_T$ and eventually reaches a minimum of 75.8 mV/decade, and rapidly increases as the gap becomes longer than 2.2 micrometer. Therefore, an optimum performance of the bio sensor can be implemented by setting the gap between the teeth of comb to 2 micrometer to 2.2 micrometer.

FIGS. 8A to 8H are schematic views illustrating a process of manufacturing a DGSC FET bio-sensor in accordance with the embodiment of the present invention. Hereinafter, the process of manufacturing the bio-sensor in accordance with the embodiment of the present invention will be described with reference to FIGS. 8A to 8H.

Figure 8A:
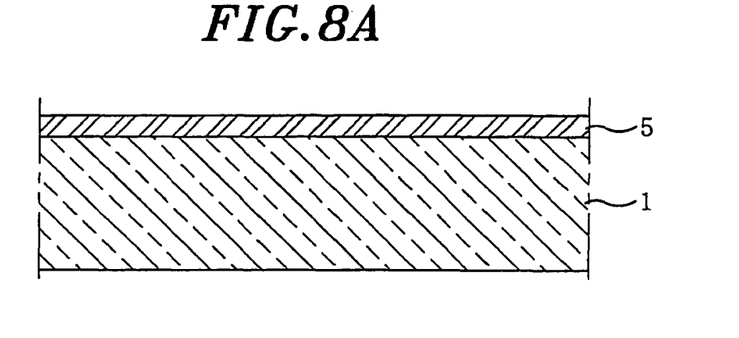
FIGS. 8A to 8H are schematic views illustrating a process of manufacturing a FET bio-sensor in accordance with an embodiment of the present invention.

As shown in FIG. 8A, the channel region 2 of the FET bio-sensor utilizing a silicon substrate and a diamond gate in accordance with the embodiments of the present invention uses an n-type silicon substrate 1 doped in a low concentration, up to $10^{15}/cm^3$ without a process of forming an n-well. The gate dielectric 5 is formed with a thickness 20 nm through thermal oxidation of a silicon oxide.

Figure 8B:
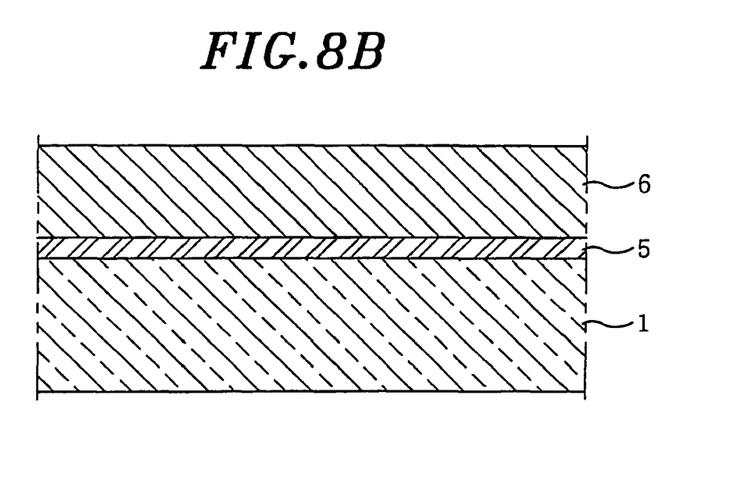

Subsequently, as shown in FIG. 8B, a conductive nano crystalline (NC) diamond thin film is chemical vapor-deposited on the gate dielectric 5 with a thickness 350 nm through the DC PECVD to be used as a gate electrode 6.

Figure 8C:
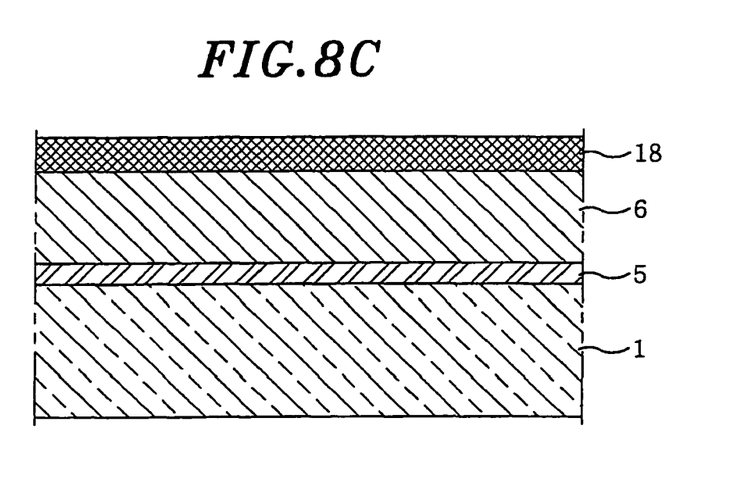

As shown in FIG. 8C, an aluminum layer 18 to be used as a diamond dry etching mask is coated to a thickness 1 nm to 100 nm by an e-beam evaporator. Thereafter, a gate of a comb shape having the size of a length L and a width W with a range from 50 micrometers to 500 micrometers respectively, and having teeth with a width and a gap of 1 micrometer to 50 micrometers is formed through photolithography of FIG. 8D.

Figure 8D:
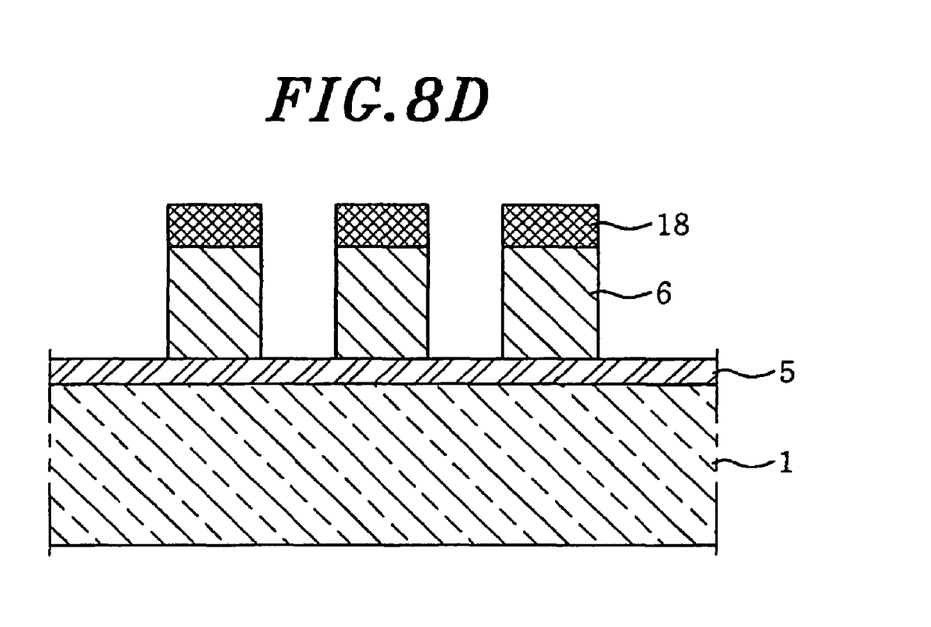

The above photolithography will be described in detail. Firstly, a photoresist is coated on the aluminum layer 18, then, the photoresist is patterned. Thereafter, the aluminum layer 18 is etched by reactive ion etching (RIE) using the pattern as a mask, thereby forming an aluminum mask. After that, the gate electrode 6 of the diamond thin film beneath the aluminum mask is etched by reactive ion etching using the aluminum mask.

Figure 8E:
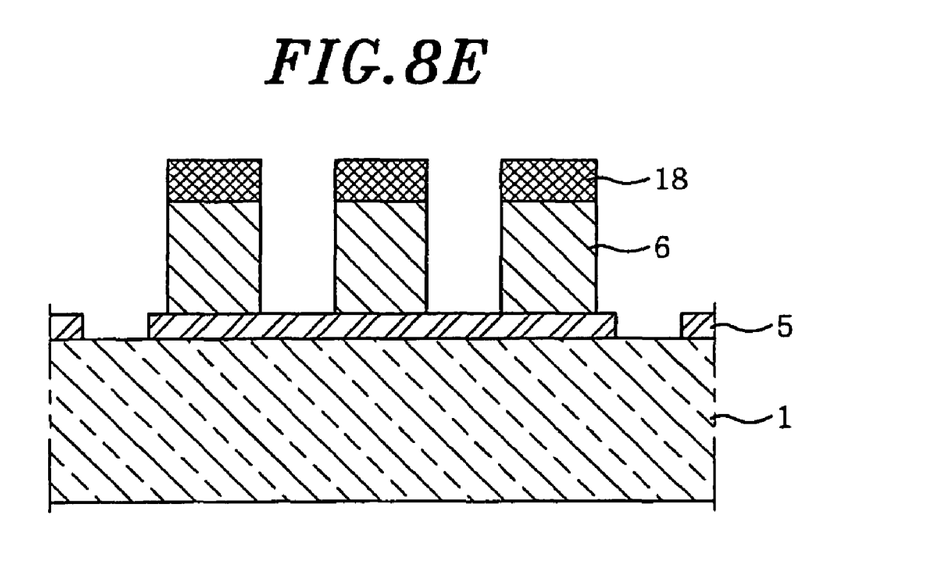
Figure 8F:
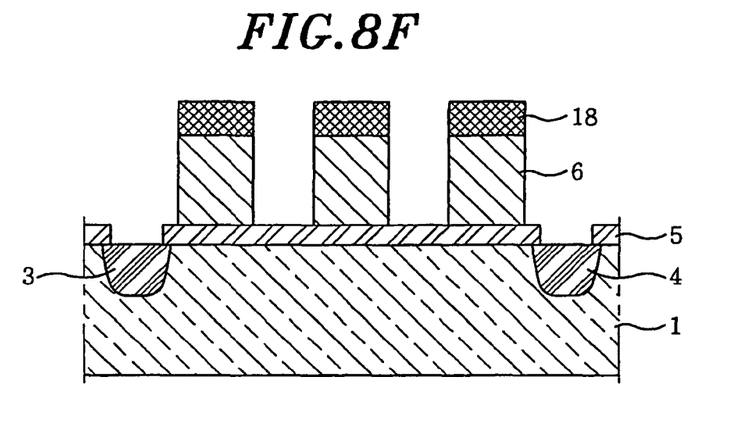
Figure 8G:
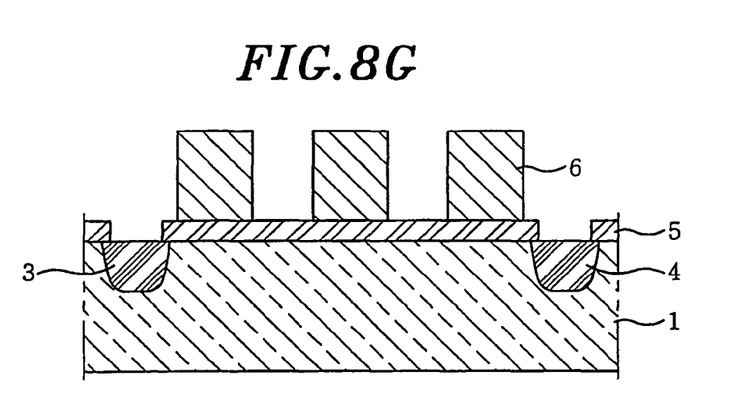
Figure 8H:
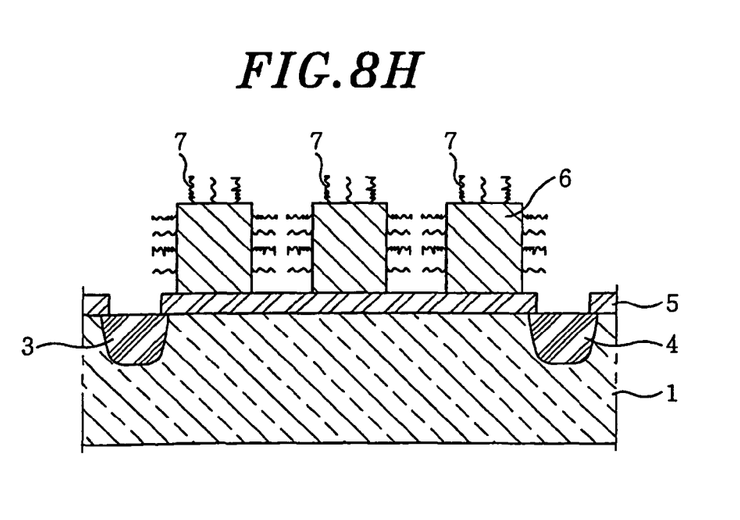

Next, as shown in FIG. 8E, regions on the silicon substrate 1 in which the source region 3 and the drain region 4 will be formed are patterned through the photolithography and the silicon oxides of the regions are removed through wet etching. Next, as shown in FIG. 8F, remaining silicon oxide and photoresist (not shown) are used as masks for doping the source region 3 and the drain region in a high concentration $10^{17}/cm^3$ using ion implantation. As shown in FIG. 8G, the remaining photoresist is removed through ashing, and the aluminum layer 18 coated on the gate electrode 6 as a mask is removed by etching. Finally, aluminum to be used as electrodes and metal lines to be connected with the external circuits for signal transfer therewith is deposited in a desired shape through a lift-off process, thereby completing the FET device. In order to provide a function of a bio-sensor to the manufactured FET device, as shown in FIG. 8h, the probe molecules 7 are attached to the surface of the gate electrode 6 of the diamond thin film.

FIGS. 9A and 9B illustrate a concept of attaching the probe molecules 7 to the surface of the gate electrode 6 of the diamond thin film. Referring to FIGS. 9A and 9B, in order to attach the probe molecules 7, the surface of the diamond thin film is treated with an H-plasma through an MW-plasma apparatus and is irradiated with ultraviolet rays for 8 hours such that 10-aminodec-1-ene to be used as probe adapter molecules 13 are attached to the surface of the diamond thin film. Since an amino group is a functional group to be bonded to the detecting molecules, the amino group is protected by protection group such as trifluoroacetamide so as not to react during the above mentioned process. After the completion of the UV reaction, the protection group is removed by hydrochloric acid and methanol, and after the removal of the protection group the detecting molecules 15 suitable to target biomolecules 16 are selected and bonded to the probe adapter molecules 13 through the linker bond or crosslinking molecules 14 to complete the probe molecules 7, resulting in manufacturing the bio-sensor.

Figure 10:
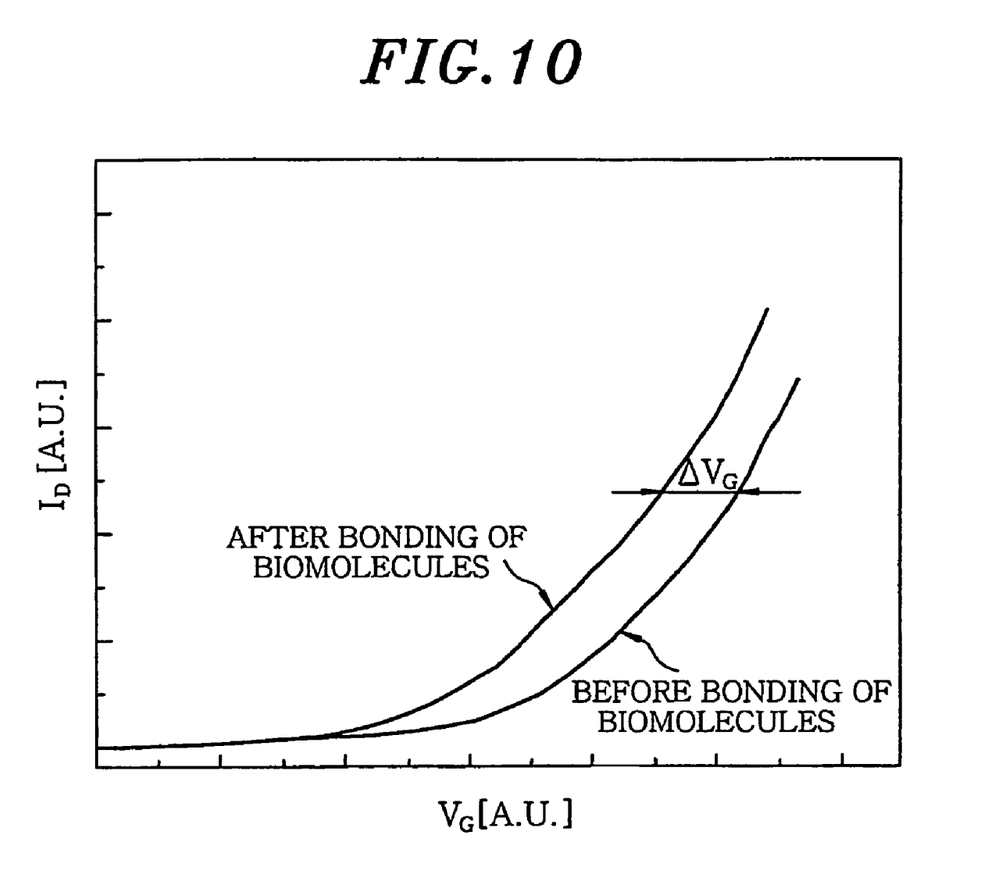
FIG. 10 is a graph illustrating a relationship between a gate voltage and source-drain current in the FET before and after bonding of the biomolecules in accordance with an embodiment of the present invention.

Hereinafter, operation of the bio-sensor manufactured with a MOSFET structure as shown in FIGS. 9A and 9B detecting DNA molecules having specific sequence will be described. In order to detect the DNA molecules having the specific sequence, thiol-terminated-cDNA molecules having complementary sequence therewith are used as the detecting molecules 15. Sulphosuccinimidyl-4-(N-maleimidomethyl)cyclohexane-1-carboxylate (SSMCC) having a hetero functional group is used as a crosslinker to produce the probe molecules 7 by bonding the detecting molecules 15 to the probe adaptor molecules 13 having an amine group. The SSMCC functions as the crosslinking molecules 14 for bonding respective amine groups and thiol groups of the probe adapter molecules 13 and the detecting molecules 15. When the gate voltage $V_G$ of $V_{th}$ (in this case, $V_{th}$=0.7 V) is applied to the prepared bio-sensor as shown in FIG. 9A and solution to be measured is poured thereon, only DNA molecules 16 having target sequence among the DNA molecules of the solution bond with the detecting molecules 15 attached to the bio-sensor. Since the DNA molecules are negatively charged biomolecules with a phosphate group back-bone, an effect of applying an additional negative gate voltage $V_G$ is provided to the MOSFET when the DNA molecules are bonded to the bio-sensor. Thus, the current $I_D$ flowing between the source and the drain varies in the relationship of $V_G$-$I_D$ in FIG. 10 and the variation of the current is measured so that the DNA molecules are detected. In other words, it is known by J. H. Yang, K. S. Song, S. Kuga, and H. Kawarada, *Characterization of Direct Immobilized Probe DNA on Partially Functionalized Diamond Solution-Gate Field-Effect Transistors*, Jpn. J. Appl. Phys., 45, L1114-L1117 (2006) that a density of from $10^{11}/cm^2$ to $10^{12}/cm^2$ of the detecting molecules 15 can be attached to the surface of the diamond when DNA with a length of 15 bp is used. When applied circumstances before and after bio-molecule bonding into a $V_G$-$I_D$ relationship of known FET theory, a $I_D$-$V_G$ curve is horizontally moved as much as $\Delta V_G$ as shown in FIG. 10 before and after biomolecular bonding. The $\Delta V_G$ of the bio-sensor in accordance with the embodiments of the present invention is calculated to be 300 mV, based on existing experimental results in one paper by W. Yang and R. J. Hamers, *Fabrication and characterization of a biologically sensitive field-effect transistor using a nanocrystalline diamond thin film*, Appl. Phys. Lett., 85(16), 3626-3628 (2004).

Next, operation of detecting a virus using the bio-sensor with MOSFET structure as shown in FIG. 9B will be described. Since virus 16' as a target biomolecules have no charge unlike DNA molecules do, a scheme similar to enzyme-linked immunosorbent assay (ELISA) method is used to generate the detection signal. Therefore, second charged probe molecules are additionally required. Firstly, antibodies against proteins of a target viruses antigen is selected as the detecting molecules 15 and is bonded to the end functional group of the probe adapter molecules 13 through the crosslinking molecules 14 to be fixed to the surface of the diamond of the bio-sensor, as in the detection of the DNA molecules. When the gate voltage $V_G$ as much as $V_{th}$ (=0.7V) is applied to the prepared bio-sensor and the solution to be measured is flowed thereon, only the target virus 16' is bound to the detecting molecules 15, i.e., the antibodies attached to the bio-sensor. However, since the captured virus molecules are not charged, the bio-sensor does not detect a signal. Thus, after flowing buffer solution thereon to clean the bio-sensor, the selected and charged second probe molecules 17 are subsequently flowed thereon. By doing so, since the viruses 16' are captured by the detecting molecules 15, the viruses 16' which are not wiped out during the cleaning are bound to the second probe molecules 17, thereby generating detection signals. A $\Delta V_G$ is measured from the generated signals, as in the case of detecting DNA molecules, using the relationship of $V_G$-$I_D$ of FIG. 10.

While the invention has been shown and described with respect to the preferred embodiments, it will be understood by those skilled in the art that various changes and modifications may be made without departing from the scope of the invention as defined in the following claims.

What is claimed is:

1. A bio-sensor comprising:
    a gate dielectric formed on a silicon semiconductor substrate;
    a gate electrode of a conductive diamond film formed on the gate dielectric, wherein the gate electrode has a lattice shape;
    probe molecules bonded on the gate electrode for detecting biomolecules;
    source/drain regions formed on the semiconductor substrate at the sides of the gate electrode; and
    diamond nano-dots formed on surfaces of the gate dielectric not covered by the gate electrode, wherein the probe molecules for detecting the biomolecules are bonded to the diamond nano-dots.

2. The bio-sensor of claim 1, wherein a length and a width of a gap between strips of the gate electrode are within a range from 50 micrometers to 500 micrometers, respectively.

3. The bio-sensor of claim 2, wherein the width of the gap of between strips of the lattice of the gate electrode ranges from 1 micrometer to 50 micrometers.

4. The bio-sensor of claim 3, wherein the width of the gap between strips of the of lattice of the gate electrode is determined such that, each extended depletion region formed below the gap between strips of the lattice after applying a gate voltage is more extended and connected to each other to form a channel by additional voltage generated when biomolecules to be measured are attached to the gate electrode.

5. The bio-sensor of claim 4, wherein the width of the gap between strips of the lattice of the gate electrode ranges from 2 micrometers to 2.2 micrometers in case a doping concentration of the substrate is $10^{15}/cm^3$.

6. The bio-sensor of claim 1, wherein the gate dielectric comprises a silicon oxide.

7. The bio-sensor of claim 1, wherein the gate dielectric comprises a high-k dielectric having a dielectric constant greater than 3.9 of a silicon oxide.

8. The bio-sensor of claim 7, wherein the gate dielectric is selected from the group consisting of silicon nitride, $HfO_2$, $ZrO_2$, $TiO_2$, and $Al_2O_3$.

9. The bio-sensor of claim 1, wherein the gate dielectric comprises a multiple layer structure in which a silicon oxide layer and a high-k dielectric having a dielectric constant greater than 3.9 of the silicon oxide are sequentially laminated.

10. The bio-sensor of claim 1, wherein the dielectric comprises hafnium silicon oxide or hafnium silicon oxide nitride composite thin film.

11. The bio-sensor of claim 1, wherein the probe molecules comprise detecting molecules for detecting target biomolecules and adapter molecules for bonding the gate electrode of the diamond thin film to the detecting molecules.

12. The bio-sensor of claim 11, wherein, in a case of the target biomolecules being charged, the target biomolecules are detected through a variation of a current between the source region and the drain region caused by charges that are generated by the bonding between the target biomolecules and the detecting molecules while a threshold voltage is applied to the gate electrode.

13. The bio-sensor of claim 12, wherein the target biomolecules comprise DNA molecules, charged biomolecules, or charged antigens.

14. The bio-sensor of claim 11, wherein, in a case of the target biomolecules being not charged, the biomolecules are detected through a variation of a current between the source region and the drain region caused by charges that are generated by the bonding between the target biomolecules bonded with the detecting molecules and second charged probe molecules after the target biomolecules are bonded to the detecting molecules while a threshold voltage is applied to the gate electrode.

15. The bio-sensor of claim 14, wherein the target biomolecules comprise uncharged biomolecules or uncharged antigens.

16. The bio-sensor of claim 15, wherein the detecting molecules comprise antibody molecules against antigen such as virus molecules and protein of viruses to be recognized as antigen.

17. A bio-sensor comprising:
    a gate dielectric of non-conductive diamond thin film formed on a silicon semiconductor substrate;
    a gate electrode formed on the gate dielectric partly exposing the gate dielectric;
    diamond nano-dots formed on surfaces of the gate dielectric not covered by the gate electrode;
    probe molecules bonded on the exposed gate electrode for detecting biomolecules wherein the probe molecules for detecting the biomolecules are bonded to the diamond nano-dots; and
    source region/drain region formed on the semiconductor substrate at the sides of the gate electrode, wherein the gate electrode is a lattice shape.

18. The bio-sensor of claim 17, wherein a gap between strips of the lattice of the gate electrode having a length and a width within a range from 50 micrometers to 500 micrometers, respectively.

19. The bio-sensor of claim 17, wherein a width of a gap between each strip of lattice of the gate electrode ranges from 1 micrometer to 50 micrometers.

20. The bio-sensor of claim 17, wherein a width of a gap between strips of the lattice of the gate electrode is determined such that each extended depletion region formed below the gap in between strips of the lattice after applying a gate voltage is more extended and connected to each other to form a channel by additional voltage generated when biomolecules to be measured are attached to the exposed gate dielectric.

21. The bio-sensor of claim 20, wherein the width of the gap between strip of the lattice of the gate electrode ranges from 2 micrometers to 2.2 micrometers in case a doping concentration of the substrate is $10^{15}/cm^3$.

22. The bio-sensor of claim 17, wherein the probe molecules comprise detecting molecules for detecting target biomolecules and adapter molecules for bonding the gate electrode of the diamond thin film to the detecting molecules.

23. The bio-sensor of claim 22, wherein, in a case of the target biomolecules being charged, the biomolecules are detected through a variation of a current between the source region and the drain region caused by charges that are generated by the bonding between the target biomolecules and the detecting molecules while a threshold voltage is applied to the gate electrode.

24. The bio-sensor of claim 23, wherein the target biomolecules comprise DNA molecules, charged biomolecules, or charged antigens.

25. The bio-sensor of claim 22, wherein, in a case of the target biomolecules being not charged, the biomolecules are detected through a variation of a current between the source region and the drain region caused by charges that are generated by the bonding between the target biomolecules bonded with the detecting molecules and second charged probe molecules after the target biomolecules are bonded to the detecting molecules while a threshold voltage is applied to the gate electrode.

26. The bio-sensor of claim 25, wherein the target biomolecules comprise uncharged biomolecules or uncharged antigens.

27. The bio-sensor of claim 26, wherein the detecting molecules comprise antibody molecules against antigen such as virus molecules and protein of viruses to be recognized as antigen.

* * * * *